United States Patent [19]

Bremer et al.

[11] Patent Number: 5,474,960
[45] Date of Patent: Dec. 12, 1995

[54] PROCESS FOR REACTIVATING A FLUID BED CATALYST IN A REACTOR DIPLEY

[75] Inventors: Noel J. Bremer, Kent; Louis R. Trott, Solon; David R. Woodbury, Bedford Hts., all of Ohio

[73] Assignee: The Standard Oil Company, Cleveland, Ohio

[21] Appl. No.: 259,814

[22] Filed: Jun. 15, 1994

[51] Int. Cl.$^6$ .............................. B01J 38/10; B01J 27/198
[52] U.S. Cl. .............................. 502/34; 502/209; 422/149
[58] Field of Search .......................... 422/139; 549/259; 502/209, 41, 45, 34

[56] References Cited

U.S. PATENT DOCUMENTS

| | | |
|---|---|---|
| 4,020,174 | 4/1977 | Partenheimer . |
| 4,089,807 | 5/1978 | Partenheimer . |
| 4,094,816 | 6/1978 | Partenheimer . |
| 4,123,442 | 10/1978 | Bakshi . |
| 4,171,316 | 10/1979 | Pederson . |
| 4,178,298 | 12/1979 | Stefani et al. . |
| 4,181,628 | 1/1980 | Stefani et al. . |
| 4,333,853 | 6/1982 | Milberger et al. . |
| 4,748,140 | 5/1988 | Blum et al. ............................ 549/259 |
| 4,795,818 | 1/1989 | Becker et al. . |
| 4,918,201 | 4/1990 | Edwards . |
| 4,940,007 | 7/1990 | Hiltunen et al. ........................ 422/139 |
| 4,950,769 | 8/1990 | McCandless et al. . |
| 5,137,860 | 8/1992 | Ebner et al. . |

FOREIGN PATENT DOCUMENTS

| | | |
|---|---|---|
| 1439489 | 6/1976 | United Kingdom . |
| 1512305 | 6/1978 | United Kingdom . |

*Primary Examiner*—Asok Pal
*Assistant Examiner*—Patrick J. Neill
*Attorney, Agent, or Firm*—Brian L. Mehosky; David J. Untener

[57] ABSTRACT

The present invention relates to improvements of fluid bed catalysts. More particularly, the present invention relates to improvements of fluid bed oxidation catalysts useful in the preparation of maleic anhydride from $C_4$ hydrocarbons, including n-butane. The present invention includes a process of contacting a fluid bed catalyst with a reactivating agent in a catalyst standpipe. The present invention also provides a catalyst containing the mixed oxides of vanadium and phosphorus, treated using the above process. The present invention further provides a process for producing maleic anhydride, utilizing the catalyst prepared using the above process. The present invention additionally provides for a reactor standpipe, utilized for regenerating catalyst according to the above process.

26 Claims, No Drawings

PROCESS FOR REACTIVATING A FLUID BED CATALYST IN A REACTOR DIPLEY

BACKGROUND OF THE INVENTION

The present invention relates to the reactivation of fluid bed catalysts. In particular, the present invention relates to on-line, in situ reactivation in reactor standpipes of fluid bed catalysts used in the petroleum, petrochemical and chemical processing industries. More particularly, the present invention relates to on-line, in situ reactivation in reactor standpipes of fluid bed oxidation catalysts useful in the preparation of maleic anhydride from $C_4$ hydrocarbons, including n-butane.

Maleic anhydride can be produced by oxidizing hydrocarbons, such as butane, butene, butadiene and benzene. Oxidation catalysts containing the mixed oxides of vanadium and phosphorus have been utilized to produce maleic anhydride from $C_4$ hydrocarbons, such as n-butane. It has been observed that as the time of reaction on the catalyst increases, the yield, activity and selectivity of the catalyst decreases. This is called "catalyst aging" or "catalyst deactivation", and is common in most catalytic processes.

The reduction in maleic anhydride yield means that more of the hydrocarbon feed is fully oxidized to carbon oxides and water; that total production of maleic anhydride declines; increased unit cost of the maleic anhydride produced; and relatively frequent catalyst replacement. Skilled workers in the art have suggested various methods of countering this loss of catalyst performance.

British Patent Specification 1,439,489 discloses regeneration of a phosphorus-vanadium-oxygen complex catalysts by discontinuing the butane feed and treating the catalyst with a reducing material such as hydrogen, carbon monoxide, methane, hydrogen sulfide, or mixtures of the same. In U.S. Pat. No. 4,123,442, sulfur trioxide was employed to partially regenerate the catalytic properties of an aged maleic anhydride catalyst. U.S. Pat. Nos. 4,020,174, 4,089, 807 and 4,094,816 disclose the use of halogens or organic halides as useful in regenerating vanadium-phosphorus catalysts. U.S. Pat. No. 4,178,298 describes activation and regeneration of fixed-bed oxidation catalysts using gaseous hydrocarbons. British Patent Specification 1,512,305 describes regenerating complex phosphorus-vanadium-oxygen catalysts by treating the aged catalyst with an aqueous solution of ammonia or amine at an elevated temperature. Many the methods described above require the removal of the deactivated catalyst from the reaction system, and all the methods require significant disruption of the production process. No known prior art describes reactivating catalyst in a fluid bed reactor standpipe.

SUMMARY OF THE INVENTION

The present invention is a process to maintain or improve the performance of fluid bed catalysts, particularly metal oxide containing catalysts, a process to produce the improved metal oxide catalyst, a process for the production of maleic anhydride, and the use of a reactor standpipe according to the above process.

The means to maintain the performance of fluid bed oxidation catalysts containing the mixed oxides of vanadium and phosphorus include a process which comprises maintaining a flow of a reactivating agent in at least one reactor standpipe and contacting the portion of the fluid bed catalyst transiting the standpipe with the reactivating agent. The term "reactivating agent" is used to denote either reactivating material, or mixtures which contain reactivating material with non-reactive or inert materials. The reactivating material may be a reducing agent, such as hydrogen, carbon monoxide, methane, hydrogen sulfide, sulfur trioxide, halogens, organic halides, ammonia, amines, hydrocarbons, or mixtures thereof. Hydrocarbons useful as reducing agents are those hydrocarbons which can be substantially volatilized at the processing conditions.

When operating a fluidized bed process, and the associated fluidized bed reactor system, catalyst must be transported into, out of, and from point to point in the reactor system. Transport of catalyst is typically achieved via pneumatic and hydraulic conveying, gravity flow, moving beds of catalyst, and the like. When transported, the channels, pipes, ducts, and the like are generically described as standpipes, particularly when oriented substantially vertically with the catalyst flowing downward. For purposes of this invention, the term "standpipe" is meant to include all channels, pipes, ducts, and the like, in whatever orientation, with stationary catalyst, or catalyst flowing in any direction. The standpipe which conveys catalyst from a reactor cyclone, filter, baghouse, or the like, back to the fluidized bed is a particular type of standpipe, and is frequently referred to as a dipleg. Catalyst reactivation can be effected when the standpipe is a dipleg for returning recovered catalyst to the fluidized bed from a cyclone, filter baghouse, and the like.

The conditions of the reactor standpipe used for reactivating the catalyst can be maintained by isolating the standpipe from the rest of the reactor system with thermal insulation and, optionally, by heating or cooling the contents of the standpipe with heating or cooling coils, heaters, the addition of supplemental heated or cooled gases, fluids, or solid heat transfer media, or combinations of the above.

The reactivating conditions in the reactor standpipe can also be maintained by the addition or exclusion of reactants from the standpipe, to permit localized concentrations and partial pressures of reactivating agents, reactivating materials, reactants, intermediates and products to differ from the concentration and partial pressures of reactivating agents, reactivating materials, reactants, intermediates and products in the fluidized bed.

In general, the present invention includes reactivating a fluid bed catalyst by contacting a catalyst containing the mixed oxides of vanadium and phosphorus with a reactivating agent in a catalyst standpipe. Additionally, the present invention includes a process for maintaining the performance of fluid bed oxidation catalysts containing the mixed oxides of vanadium and phosphorus, which comprises removing a portion of the fluid bed catalyst from the reaction zone of a fluidized bed to at least one reactor standpipe, contacting the portion of the fluid bed catalyst in the standpipe with a reactivating agent, and returning the fluid bed catalyst to the reaction zone of said fluidized bed. The present invention also provides a fluidizable catalyst containing the mixed oxides of vanadium and phosphorus, reactivated by the above process. The present invention further provides a process for producing maleic arthydride, utilizing the catalyst reactivated by the technique described above.

DETAILED DESCRIPTION OF THE INVENTION

We have found that fluid bed catalysts can be regenerated in situ by contacting the catalyst with a flow of a reactivating agent in a reactor standpipe. In particular, we have found that fluid bed maleic anhydride catalysts containing the mixed oxides of vanadium and phosphorus can be regenerated in situ by contacting the fluid bed catalyst with a flow of a reactivating agent in a reactor standpipe.

In operating a fluid bed reactor, process gas typically enters a plenum beneath a bed-supporting grid, and then bubbles up through the solid bed material, fluidizing the material. The gas exits the bed and entrains a portion of the solid bed material in the gas stream. The entrained solids are separated from the gas stream, typically using a filter, baghouse, or cyclone separator. The separated catalyst is returned to the bed of solid material using a substantially vertical standpipe via gravity flow. Supplemental gas is frequently injected into the standpipe to partially fluidize the flowing solids, and increase flow through the standpipe. Although the flow of solid material inside a fluid bed reactor vessel may vary depending upon the specific operating characteristics of the vessel, solids material and gas flow rates, the flow of solid bed material through the standpipe is quite significant. The entire contents of the bed of solid material may be conveyed through the standpipe one or more times every hour of reactor operation.

It is the purpose of the present invention to exploit the flow of bed material and regenerate the bed material in situ while maintaining reactor operation. By maintaining conditions conducive to regeneration of the catalyst bed material in one or more standpipe, incremental regeneration of the catalyst, or "polishing" of the catalyst, can be achieved with minimal disruption to the production process. Also, since the reactivating or polishing may be continuously effected upon a constantly changing portion of the catalyst bed material, the overall performance of the catalyst bed may be maintained for an extended period.

In addition to the overall improved performance of the catalyst bed system, numerous other benefits are realized. If operated in a continuous manner, less severe conditions are required to regenerate the bed material because the catalyst material is not appreciably deactivated before reactivating. The standpipe system can contain corrosive or harmful materials permitting the use of such material in a reactor system otherwise incompatible due to metallurgical or other constraints. Further, the materials used in the process, or the byproducts resulting from the practice of the invention, constitute only a fraction of the total effluent gas from the fluid bed reactor, and the neutralization, recovery or disposal of the diluted material may be accommodated by existing equipment.

The required reactivating temperature is maintained by the heat in the fluid bed surrounding the standpipe and control of the relative flow rates of catalyst and reactivating agent. Alternately, the standpipe may be insulated to isolate the standpipe from the reactor temperature, and supplemental heating or cooling provided. Methods for introducing additional heat are well known in the art and include, but are not limited to, the use of internal heaters, steam coils, altering the temperature, composition and flow rate of the supplemental gas to effect full or partial combustion, and the like. Cooling can be provided in a like manner, using cooling coils, heat pipes, supplemental cooling gas, introducing cooled solids and fluids to the reactivating zone, and the like.

Localized processing conditions can thus be modified and controlled. Due to the significantly smaller size of the standpipe relative to the total fluidized bed, specialized materials of construction, otherwise too expensive, may be employed, as well as temperatures and reactant concentrations which would be uneconomical for the entire reactor unit. Additionally, the total mass of the catalyst being reactivated is substantially less than the mass of the fluidized bed, and much more precise control of the reactivating parameters, i.e., temperature, pressure, compositions, flow rates, etc., can be maintained. Further, reactivating within a standpipe permits isolating the reactivating zone from the fluidized bed without the use of any additional equipment. Utilization of the present invention is particularly desirable in existing fluid bed reactor systems, as no significant modification of the existing reactor is required.

Catalysts for the production of maleic anhydride from $C_4$ hydrocarbons, such as n-butane, butenes, and butadiene, particularly n-butane, generally contain the mixed oxides of vanadium and phosphorus. The catalysts may additionally contain promoter elements, including but not limited to alkali or alkaline earth metals, titanium, zirconium, hafnium, niobium, molybdenum, iron, cobalt, nickel, copper, zinc, cadmium, rare earths, cerium, uranium and mixtures thereof. The molar ratio of promoter elements to vanadium is generally 0.001:1 to 1:1, preferably about 0.1:1 to 0.5:1. The molar ratio of phosphorus to vanadium is generally about 0.5:1 to about 2:1, preferably about 0.9:1 to about 1.6:1. The valence of the vanadium component of the catalyst is generally reduced from the pentavalent state, the valence of vanadium generally being between about 3.5 to about 4.6 and preferably being about 4. The maleic anhydride catalyst may additionally contain diluents or supports, such as titania, alumina, alumina-silica, zirconia, silica, silicon carbide, and the like.

The catalysts may be prepared by reacting catalyst component containing compounds in the presence or absence of a corrosive reducing material in a liquid, including but not limited to water, alcohols, aldehydes, glycols, ketones, halogenated olefins, and the like. Suitable corrosive reducing materials to provide vanadium in the proper valence state include but are not limited to HCl, HBr, and oxalic acid. Suitable liquid media capable of reducing vanadium to its proper valence state include but are not limited to isopropanol, isobutanol, crotyl alcohol, allyl alcohol, isopentanol, acetaldehyde, propionaldehyde, butyraldehyde, ethylene glycol, methyl ethyl ketone, perchloropropene, hexachlorobutadiene and the like.

Suitable vanadium compounds for use in preparing the maleic anhydride catalysts include vanadium pentoxide or vanadium salts, such as ammonium metavanadate and vanadium oxytrihalides. Suitable phosphorus containing compounds include phosphoric acid, metaphosphoric acid, orthophosphoric acid, triphosphoric acid and pyrophosphoric acid, phosphorus pentoxide, phosphorus oxyiodide, phosphorus oxychloride, phosphorus pentachloride, and the like. Suitable promoter element containing compounds include promoter metal oxides, hydroxides, nitrates, halides, or salts of organic acids such as acetates, formates, buryrates, benzylates, and the like.

The catalyst components are mixed in the liquid medium, before or after the vanadium component is reduced to its proper valence state. The catalyst precursor formed is recovered and dried. The catalyst is formed into fluid bed form by crushing and screening the catalyst particles to a proper size, such as in the range of about 20 to about 300 microns, by the oil drop method, wherein an aqueous solution or slurry of the catalyst is dropped into a heated oil bath to form solid particles, or by spray drying to form the desired particles. The catalyst may be calcined before or after forming into the fluidizable particles, dependent upon the method of preparation chosen. A method of preparing fluidizable catalysts containing mixed oxides of vanadium and phosphorus useful for the production of maleic anhydride from $C_4$ hydrocarbons such as n-butane is disclosed in U.S. Pat. No. 4,317,778 assigned to our common assignee, incorporated herein by reference.

Methods for activating, or increasing the catalytic activity of the catalyst are described in the literature. U.S. Pat. No. 4,171,316 describes a method to "condition" vanadium phosphate-containing catalyst.

In the process described in U.S. Pat. No. 4,748,140, assigned to our common assignee, and incorporated herein by reference, fluidizable catalysts containing the mixed oxides of vanadium and phosphorus are activated by contacting the catalyst with oxygen and a reducing gas at least partially combustible with oxygen at an elevated temperature sufficient to cause such combustion, in a molar ratio of reducing gas to oxygen greater than the stoichiometric ratio required for complete combustion of the reducing gas.

Hydrocarbons reacted to form maleic anhydride include n-butane, butenes, butadiene, or a mixture thereof. The molecular oxygen used in the reaction is most conveniently added as air, but synthetic streams containing molecular oxygen are also suitable. In addition to the hydrocarbon and molecular oxygen, other gases may be added to the reactant feed, such as steam or nitrogen. Preferably, oxygen-hydrocarbon ratios in the reactor feed are about 4 to about 20 moles of oxygen per mole of hydrocarbon.

The specific method of preparing or activating the catalyst is not, however, critical to the process of the present invention.

The conditions for reactivating the catalyst may vary, and are dependent upon the particular reactivating agent and catalyst employed. A minimum temperature of about 300° C. is preferred, a minimum temperature of about 375° C. more preferred, and a minimum temperature of about 400° C. most preferred. A maximum temperature of about 700° C. is preferred, a maximum temperature of about 625° C. more preferred, and a maximum temperature of about 500° C. most preferred.

The reactivating period may also vary in duration, depending upon the catalyst composition, catalyst size distribution, reactant flow rates, the reactivating agent selected, and the reactor geometry. A minimum reactivating period of about 1 second is preferred, a minimum reactivating period of about 5 seconds more preferred, and a minimum reactivating period of about 10 seconds most preferred. A maximum reactivating period of about 20 minutes is preferred, a maximum reactivating period of about 5 minutes more preferred, and a maximum reactivating period of about 1 minute most preferred.

A reactivating atmosphere in the standpipe may be maintained by the use of a reactivating agent containing materials selected from the group consisting of hydrogen, carbon monoxide, methane, hydrogen sulfide, sulfur trioxide, halogens, organic halides, ammonia, amines, hydrocarbons, and mixtures thereof. Non-reactive or inert materials may be added to the reactivating agent as a diluent, or for other processing considerations, such as maintaining appropriate solids fluidization, temperature, pressure, or to control the partial pressure of the reactivating agent, reactivating materials, reactants, intermediates and products.

The rate of introduction of the reactivating agent may be varied. A rate of introduction sufficient to maintain the catalyst in a dilute fluidize phase in the standpipe is preferred, a rate sufficient to fluidize the catalyst in the standpipe, but not substantially elutriate catalyst from the standpipe more preferred, and a rate sufficient to maintain the catalyst at a point of incipient fluidization, i.e., the lowest superficial fluid velocity at which the pressure drop across the bed equals the weight of the bed charge per unit area, most preferred. A dilute fluidized phase exists when the void fraction, defined as the fraction of fluidized phase not occupied by solids, exceeds 90 percent. The rate of introduction of the reactivating agent may also be varied as dictated by other processing considerations.

The reactivating process may be conducted at atmospheric, superatmospheric or subatmospheric pressure, although operation at superatmospheric pressure is preferred, and operation at 15 to 30 psia most preferred.

CATALYST REGENERATION

Typically, standpipes have aspect ratios greater than about 7, more typically greater than 12. The standpipe aspect ratio is the ratio of the standpipe length divided by the hydraulic diameter. The hydraulic diameter is defined as the standpipe cross-sectional area divided by one-half (1/2) the standpipe perimeter "wetted" by, i.e., in contact with, the material inside the standpipe.

As described previously, in operating a fluid bed reactor, solids entrained from the fluidized bed are separated from the gas stream, typically using a filter, baghouse or cyclone separator. The separated catalyst is returned to the bed of solid material using a substantially vertical standpipe via gravity flow, sometimes known as a dipleg. Supplemental gas is frequently injected into the standpipe to partially fluidize the flowing solids, and increase flow through the standpipe.

The flow of solid bed material through the standpipe is quite significant. The entire contents of the bed of solid material may be conveyed through the standpipe one or more time every hour of reactor operation. A particular catalyst particle may reside in the standpipe for a period of a second or less, a number of minutes, or for an hour or more, depending upon reactor operation. If catalyst is permitted to flow to the bed of solid material under gravity flow with little or no supplemental fluidizing gas, catalyst residence time can be calculated by dividing the volumetric flow rate of catalyst by the cross-sectional area of the return standpipe. Typical catalyst residence times in such a situation would range from about 10 seconds to about 1 minute. If, however, sufficient supplemental fluidizing gas is added to the standpipe, the residence time of a particular catalyst particle can be significantly shorter or longer, as the fluidizing gas circulates the catalyst particles within the standpipe. Residence times are then best evaluated on a statistical basis. Use of a continuous, stirred-tank reactor (CSTR) model is one approach. Typical catalyst residence times would be in the range from about 1 second to about 20 minutes.

While present in the reactor standpipe, localized conditions surrounding the catalyst can be modified and controlled. Temperature, atmosphere and, to a lesser extent, pressure can be significantly different from that of the bed of fluidized solid material. The standpipe may optionally be constructed of a material better suited to catalyst reactivating than the material used to construct the rest of the reactor, and supplemental heating and cooling equipment may be incorporated into the standpipe, as well as insulation to further isolate the catalyst in the standpipe from the general reactor conditions.

Additionally, reactant concentrations and compositions may be selected which would be otherwise impracticable in the fluid bed reactor system. As the standpipe cross-section may be several orders of magnitude smaller than the cross-section of the fluid bed reactor, reactant concentrations too high or low for the total reactor may be utilized. High concentrations, in particular, can exploit the additional benefit of later dilution by the bulk reactor gases, with the potential of utilizing standard processing equipment elsewhere in the reactor system.

Specifically, catalyst particles traversing a standpipe from the effluent cyclones, filter, baghouse or the like, can be processed to maintain the performance of the catalyst bed. A reactivating agent containing material such as hydrogen, carbon monoxide, methane, hydrogen sulfide, sulfur trioxide, halogens, organic halides, ammonia, amines, hydrocarbons, mixtures thereof, and the like can be introduced to the standpipe, and thus into contact with the catalyst contained therein.

Typically, a gaseous reactivating agent is used, and is introduced to the standpipe near the bottom, discharge opening. Diluents of inert or non-reactive material, as described previously, may also be introduced to the standpipe, either mixed with the reactivating agent, or separately at the same or different location. The gaseous reactivating agent percolates upwards through the descending catalyst, and exits the top of the dipleg. In those instances where the standpipe is a catalyst return, sometimes called a dipleg, from a cyclone, filter, baghouse, or the like, the gaseous reactivating agent exits the standpipe/dipleg into the cyclone, baghouse, etc., mixes with the bulk reactor effluent, and exits the reactor.

If sufficient gaseous reactivating agent is introduced to the standpipe, the reactivating agent may actually fluidize the catalyst, with the potential of increasing catalyst flow rates through the standpipe, as well as increased partial pressure of the reactivating agent in contact with the catalyst particles. If small quantities of reactivating agent are required, the reactivating agent may be introduced near the top of the standpipe, and travel cocurrently with the descending catalyst, exiting the bottom of the standpipe into the main catalyst bed.

If necessary, additional materials, heated or cooled as required, may also be introduced to the standpipe to alter or control the reactivating temperature within the standpipe. If the standpipe is heated or cooled, additional insulation between the standpipe and the fluidized bed of solid material may optionally be utilized. Other methods of heating or cooling the standpipe contents, including circulating coolants, heated oil, steam, or the use of resistance heating, are well known in the art.

Reactivated catalyst is discharged back to the fluidized bed. By the process of elutriation, the catalyst is subsequently transported out of the fluidized bed and back to cyclone, filter, baghouse, etc., and returned to the standpipe for more reactivating.

The invention is equally applicable to other fluid bed processes including, but not limited to, $C_3$ ammoxidation, $C_3$ oxidation to acrylic acid, $C_3$ ammoxidation to acrylonitrile, xylene oxidation to phthalic anhydride plus maleic anhydride, olefin polymerization, and the like.

SPECIFIC EMBODIMENTS

EXAMPLE 1

The Test Apparatus

A test reactor was used to simulate the catalyst reactivation of the present invention. A fluidizable catalysts was used to produce maleic anhydride from n-butane in a fluid bed test reactor consisting of about a 61 cm length of stainless steel tubing having an inner diameter of about 3.8 cm, having a stainless steel sparget at the bottom of the tube to act as a gas (air) distributor with an axial 0.64 cm outer diameter thermowell and a separate hydrocarbon inlet at the bottom of the tube. The reactor was fitted with internal gas redistributing baffles. Gas heating and reactor temperature control was accomplished by placement of the reactor unit in a thermostatic fluidized sand bath.

Flasks for receiving the product maleic anhydride were cooled, and effluent gases were routed to a gas chromatograph for analysis. Reaction conditions and results of the tests run are described in the tables below. The throughput of hydrocarbon feed in the production of maleic anhydride, or the working rate imposed upon the catalyst can be described as WWH, or weight of feed/weight of catalyst/hour.

The Test Catalyst

A catalyst containing the mixed oxides of vanadium and phosphorus, having a phosphorus to vanadium ratio of 1.2:1 were prepared as described in U.S. Pat. No. 4,317,778, incorporated by reference above. The catalyst was aged in a separate, larger reactor for a period of at least 10,000 hours. During the aging, the catalyst activity diminished, with resulting lower yield, conversion and selectivity. Samples of the catalyst were withdrawn from the larger reactor and cooled to ambient temperature. Individual samples of the catalyst were then introduced to the test apparatus, and the performance of the catalyst evaluated. Performance data for aged catalyst is presented in Table I.

TABLE I

| TYPICAL AGED CATALYSTS PRIOR TO REACTIVATION | | |
|---|---|---|
| SAMPLE | APPROXIMATE TIME ON STREAM (HOURS) | YIELD (SINGLE PASS) MALEIC ANHYDRIDE (%) |
| A | 10,000 | 48.3 |
| B | 12,000 | 48.7 |
| C | 13,000 | 48.3 |
| D | 14,500 | 45.7 |

Reactivating Tests

The aged catalyst was run in the test reactor at the conditions indicated in Table II for 2 hours to equilibrate the system at standard test conditions, and the catalyst performance determined. The operating conditions and results are reported as Example 1a, in Table II, below. The operating conditions were maintained for an additional 22 hours. The butane and air flows were then discontinued, and a reactivating agent introduced to the reactor bed through the butane sparger. For Example 1, the reactivating agent consisted of gaseous mixture of 33 parts nitrogen and 1 part n-butane at a rate to maintain a WWH at 0.05. Simultaneously, the reactor temperature was adjusted to 480° C., and the reactivating process continued for 4 hours, as indicated in Table II. Flow of the reactivating agent was then discontinued, the standard butane and air flows re-established, and the reactor temperature readjusted to standard test conditions. The reactor was then permitted to equilibrate for the periods indicated in the Table (for 19 hours for the first post-process test, Example 1b; 47 total hours on-stream), and subsequent performance data, Examples 1c–11, collected.

Reaction and processing conditions, and results for Example 1 and the following examples are contained in the table below. The results are stated in the following terms:

$$\% \text{ Single Pass Yield} = \frac{\text{Moles of Maleic Anhydride Formed} \times 100}{\text{Moles of Butane Fed}}$$

$$\% \text{ Conversion} = \frac{\text{Moles of Butane Reacted} \times 100}{\text{Moles of Butane Fed}}$$

$$\% \text{ Selectivity} = \frac{\% \text{ Single Pass Yield} \times 100}{\% \text{ Conversion}}$$

EXAMPLES 2–5

Separate samples of the catalysts prepared and aged according to Example 1 were introduced to the test apparatus. All samples were typical of aged catalyst, had at least 10,000 hours of operating history, and single pass yields to maleic anhydride of 48.7%, possibly as low as 45.7%, corresponding to the data of Table I.

The catalysts were used to produce maleic anhydride by n-butane oxidation, and reactor conditions equilibrated for the time indicated in the Table. The catalyst samples were reactivated for the period and at the conditions indicated below, and then reaction feeds of 1 mole of butane to 33 moles of air were initiated for the production of maleic anhydride.

Reactivating conditions for Examples 2 through 5 were as follows:

EXAMPLE 2

The aged catalyst was processed at 350° C. for 4 hours at a WWH of 0.05, with a reactivating agent blend of 33 part nitrogen to 1 part propylene.

EXAMPLE 3

The aged catalyst was processed at 616° C. for 1 hour at a WWH of 0.05, with a reactivating agent blend of 33 part nitrogen to 1 part n-butane.

TABLE II

| EXAMPLE NUMBER | HOURS AT 0.05 WWH | BED TEMP (C.) | % YIELD (SINGLE PASS) | % CONVERSION | % SELECT | % CO | % CO2 | AIR/HC RATIO | % EFFL. OXYGEN |
|---|---|---|---|---|---|---|---|---|---|
| 1a | 2 | 413 | 49.4 | 81.4 | 60.7 | 15.9 | 14.8 | 33/1 | 9.4 |
| Reactivating | 24–28 | 480 | | | | | | | 0.0 |
| 1b | 47 | 414 | 58.2 | 90.8 | 64.1 | 16.5 | 14.8 | 33/1 | 9.0 |
| 1c | 52 | 413 | 58.1 | 89.8 | 64.7 | 16.1 | 14.3 | 33/1 | 9.1 |
| 1d | 70 | 413 | 57.5 | 88.9 | 64.7 | 15.9 | 14.2 | 33/1 | 9.4 |
| 1e | 93 | 415 | 58.5 | 90.7 | 64.5 | 16.4 | 14.4 | 33/1 | 9.3 |
| 1f | 164 | 417 | 58.1 | 89.9 | 64.7 | 16.3 | 14.4 | 33/1 | 9.3 |
| 1g | 194 | 418 | 56.7 | 89.8 | 63.1 | 17.0 | 14.8 | 33/1 | 9.3 |
| 1h | 213 | 419 | 56.9 | 89.9 | 63.2 | 16.8 | 14.9 | 33/1 | 9.0 |
| 1i | 239 | 418 | 56.3 | 89.6 | 62.9 | 16.8 | 15.2 | 33/1 | 9.2 |
| 1j | 263 | 420 | 55.8 | 89.5 | 62.4 | 17.0 | 15.3 | 33/1 | 9.1 |
| 1k | 336 | 421 | 55.3 | 89.3 | 62.0 | 17.1 | 15.5 | 33/1 | 9.1 |
| 1l | 383 | 422 | 56.2 | 90.0 | 62.4 | 17.1 | 15.3 | 33/1 | 9.2 |
| 2a | 25 | 428 | 52.3 | 90.6 | 57.7 | 20.1 | 17.2 | 33/1 | 7.9 |
| 2b | 72 | 427 | 52.0 | 90.0 | 57.8 | 19.9 | 17.1 | 33/1 | 8.2 |
| 3a | 30 | 429 | 54.2 | 89.6 | 60.5 | 19.9 | 15.5 | 33/1 | 8.4 |
| 3b | 49 | 428 | 55.7 | 89.1 | 62.5 | 18.2 | 14.1 | 33/1 | 8.6 |
| 3c | 73 | 429 | 55.4 | 89.3 | 62.1 | 18.4 | 14.4 | 33/1 | 8.6 |
| 3d | 96 | 429 | 55.2 | 89.5 | 61.6 | 18.5 | 14.7 | 33/1 | 8.6 |
| 3e | 145 | 429 | 54.4 | 90.3 | 60.2 | 19.3 | 15.6 | 33/1 | 8.4 |
| 3f | 168 | 429 | 54.0 | 88.7 | 60.9 | 18.4 | 15.3 | 33/1 | 8.6 |
| 3g | 170 | 430 | 54.2 | 89.6 | 60.5 | 18.9 | 15.4 | 33/1 | 8.5 |
| 3h | 197 | 429 | 55.1 | 89.9 | 61.3 | 18.8 | 15.1 | 33/1 | 8.5 |
| 3i | 216 | 430 | 54.5 | 90.0 | 60.6 | 18.9 | 15.6 | 33/1 | 8.4 |
| 3j | 244 | 430 | 54.9 | 90.5 | 60.6 | 19.1 | 15.5 | 33/1 | 8.4 |
| 3k | 263 | 430 | 54.2 | 90.6 | 59.8 | 19.2 | 16.2 | 33/1 | 8.3 |
| 3l | 266 | 430 | 54.6 | 90.6 | 60.3 | 19.2 | 15.7 | 33/1 | 8.4 |
| 3m | 314 | 430 | 53.9 | 90.7 | 59.4 | 19.3 | 16.4 | 33/1 | 8.3 |
| 3n | 337 | 430 | 54.2 | 91.0 | 59.5 | 19.5 | 16.2 | 33/1 | 8.3 |
| 3o | 360 | 430 | 54.2 | 91.2 | 59.4 | 19.8 | 16.2 | 33/1 | 8.2 |
| 3p | 383 | 428 | 53.7 | 90.3 | 59.5 | 19.2 | 16.2 | 33/1 | 8.3 |
| 3q | 408 | 428 | 53.8 | 90.2 | 59.7 | 19.2 | 16.1 | 33/1 | 8.3 |
| 3r | 432 | 428 | 53.8 | 90.5 | 59.5 | 19.4 | 16.2 | 33/1 | 8.3 |
| 3s | 505 | 428 | 53.8 | 90.9 | 59.2 | 19.6 | 16.4 | 33/1 | 8.3 |
| 3t | 530 | 428 | 53.6 | 90.7 | 59.1 | 19.5 | 16.6 | 33/1 | 8.3 |
| 4a | 22 | 431 | 54.8 | 89.5 | 61.2 | 18.6 | 15.0 | 33/1 | 8.9 |
| 4b | 43 | 432 | 54.5 | 88.9 | 61.3 | 18.4 | 14.8 | 33/1 | 8.9 |
| 4c | 70 | 435 | 54.2 | 90.2 | 60.1 | 19.2 | 15.7 | 33/1 | 8.7 |
| 4d | 91 | 435 | 54.5 | 90.2 | 60.4 | 19.2 | 15.5 | 33/1 | 8.8 |
| 4e | 164 | 434 | 54.2 | 90.2 | 60.1 | 19.2 | 15.6 | 33/1 | 8.8 |
| 4f | 210 | 433 | 54.2 | 90.3 | 60.0 | 19.3 | 15.7 | 33/1 | 8.9 |
| 5a | 45 | 431 | 54.8 | 90.5 | 60.6 | 18.7 | 16.0 | 33/1 | 8.8 |
| 5b | 93 | 431 | 53.9 | 90.1 | 59.8 | 18.8 | 16.5 | 33/1 | 8.5 |

TABLE II-continued

| | | | REACTIVATED CATALYST | | | | | | |
|---|---|---|---|---|---|---|---|---|---|
| EXAMPLE NUMBER | HOURS AT 0.05 WWH | BED TEMP (C.) | % YIELD (SINGLE PASS) | % CONVERSION | % SELECT | % CO | % CO2 | AIR/HC RATIO | % EFFL. OXYGEN |
| 5c | 159 | 432 | 53.8 | 90.6 | 59.4 | 19.1 | 16.8 | 33/1 | 8.5 |

EXAMPLE 4

The aged catalyst was processed at 616° C. for 1 hour at a WWH of 0.05, with a reactivating agent blend of 33 part nitrogen to 1 part n-butane.

EXAMPLE 5

The aged catalyst was processed at 600° C. for 1 hour at a WWH of 0.05, with a reactivating agent blend of 18 part nitrogen to 1 part hydrogen.

The reactivation of the catalyst may be carried out continuously. Reactivating times of 1 to 4 hours were used in the examples to simulate total reactivating time of a typical fluid bed catalyst circulated numerous times through a cyclone dipleg, similar to typical commercial operation in a fluidized bed reactor system. For example, a fluidized bed system that, on average, circulated the entire catalyst bed through the cyclones twice an hour with an average 2 minute residence time in the cyclone dipleg per cycle would be equivalent to 1.6 hours of reactivating every 24 hours of reactor operation.

The invention thus permits the maintenance of a high level of activity in the reactor catalyst bed by continuously introducing freshly reactivated catalyst to the main catalyst bed. However, if operation or economic considerations so dictate, the process can also be carried out periodically, or only when performance of the catalyst has diminished to a selected level.

Thus it should be apparent to those skilled in the art that the subject invention can be utilized for any fluid bed catalyst capable of being reactivated by being contacted with a reactivating agent. Applicants' invention is directly applicable to fluid bed catalytic processes in the petroleum, petrochemical and chemical processing industries. Specific applications include, but are not limited to, fluid catalytic cracking of petroleum, fluid catalytic reforming, fluid catalytic oxidation of ethylene, fluid bed synthesis of alkyl chlorides, fluid bed hydrocarbon synthesis, fluid bed synthesis of phthalic anhydride, fluid bed synthesis of acrylonitrile, and the like.

It should be further apparent to those skilled in the art that the subject invention accomplishes the purposes set forth above. It is to be understood that the subject invention is not to be limited by the examples set forth herein. These have been provided merely to demonstrate operability, and the selection of methods of preparation of the vanadium and phosphorus mixed oxide containing catalysts, the hydrocarbon feedstocks, the reactivating feeds, reactivating agents, molar ratios, and reaction and reactivating conditions can be determined from the total specification disclosure provided without departing from the spirit of the invention herein disclosed and described, the scope of the invention including equivalent embodiments, modifications and variations that fall within the scope of the attached claims.

We claim:

1. A process for maintaining the performance of fluid bed oxidation catalysts containing the mixed oxides of vanadium and phosphorus, which comprises:

(a) removing a portion of said fluid bed catalyst from the reaction zone of a fluidized bed to at least one reactor dipleg;

(b) contacting said portion of the fluid bed catalyst in said dipleg with a reactivating agent; and (c) returning said fluid bed catalyst from said dipleg to the reaction zone of said fluidized bed.

2. The process as in claim 1 wherein said reactivating agent contains a reducing agent.

3. The process as in claim 2 wherein said reducing agent is selected from the group consisting of hydrogen, carbon monoxide, methane, hydrogen sulfide, sulfur trioxide, halogens, organic halides, ammonia, amines, hydrocarbons, and mixtures thereof.

4. The process as in claim 1 wherein said reactivating agent is diluted with non-reactive or inert materials.

5. The process as in claim 1 wherein said dipleg is thermally isolated from the fluidized bed.

6. The process as in claim 1 wherein said fluid bed catalyst in said dipleg is maintained at a temperature higher than the fluidized bed by supplemental heating.

7. The process as in claim 6 wherein said supplemental heating is effected using a heating method selected from the group consisting of heating coils, resistance heaters, heated gas, circulation of heated solids, combustion in said dipleg, and combinations of the same.

8. The process as in claim 1 wherein said fluid bed catalyst dipleg is maintained at a temperature lower than the fluidized bed by supplemental cooling.

9. The process as in claim 8 wherein said supplemental cooling is effected using a cooling method selected from the group consisting of cooling coils, cooling gas, circulation of cooled solids, phase change of material in said dipleg, and combinations of the same.

10. The process as in claim 1 wherein the concentration in said dipleg of reactants and products are maintained at a concentration different from the reactant and product concentration in the fluidized bed.

11. The process as in claim 1 wherein the pressure inside said dipleg is maintained at a pressure different from the pressure in the fluidized bed.

12. The process as in claim 1 wherein the temperature of said fluid bed catalyst in said dipleg is from about 300° C. to about 700° C.

13. The process as in claim 1 wherein the temperature of said fluid bed catalyst in said dipleg is from about 375° C. to about 625° C.

14. The process as in claim 1 wherein the temperature of said fluid bed catalyst in said dipleg is from about 400° C. to about 500° C.

15. The process as in claim 1 wherein said reactivating agent contacts said fluid bed catalyst for a period from about 1 second to about 20 minutes.

16. The process as in claim 1 wherein said reactivating agent contacts said fluid bed catalyst for a period from about 5 seconds to about 5 minutes.

17. The process as in claim 1 wherein said reactivating agent contacts said fluid bed catalyst for a period from about 10 seconds to about 1 minute.

18. The process as in claim 1 wherein reactivating agent is introduced to said dipleg at a rate to maintain said fluid bed catalyst in a dilute fluidized phase.

19. The process as in claim 1 wherein reactivating agent is introduced to said dipleg at a rate sufficient to fluidize said fluid bed catalyst in said dipleg, but not substantially elutriate said fluid bed catalyst from said dipleg.

20. The process as in claim 1 wherein reactivating agent is introduced to said dipleg at a rate sufficient to maintain said fluid bed catalyst at a point of incipient fluidization.

21. A mixed metal oxide catalyst whose preparation includes the process of claim 1.

22. A process for the production of maleic anhydride utilizing a catalyst whose preparation includes the process of claim 1.

23. A fluid bed reactor dipleg, utilized for regenerating catalyst according to the process of claim 1.

24. A process for maintaining the performance of fluid bed catalysts which comprises:

(a) maintaining a flow of a reactivating agent in at least one reactor dipleg; and (b) contacting the portion of the fluid bed catalyst transiting said dipleg with said reactivating agent.

25. A fluid bed catalyst whose preparation includes the process of claim 24.

26. A fluid bed reactor dipleg, utilized for regenerating catalyst according to the process of claim 24.

* * * * *

UNITED STATES PATENT AND TRADEMARK OFFICE
CERTIFICATE OF CORRECTION

PATENT NO. : 5,474,960
DATED : December 12, 1995
INVENTOR(S) : Noel J. Bremer, et al.

It is certified that error appears in the above-identified patent and that said Letters Patent is hereby corrected as shown below:

On the title page, item [54] and Col. 1, line 2,
Delete the last word of the title of the patent "Dipley" and substitute --Dipleg--.

In claim 8, column 12, line 39, after the word "catalyst", insert the words --in said--.

Signed and Sealed this

Fifth Day of March, 1996

Attest:

BRUCE LEHMAN

Attesting Officer

Commissioner of Patents and Trademarks